(12) United States Patent
Niznick

(10) Patent No.: US 8,118,596 B2
(45) Date of Patent: Feb. 21, 2012

(54) ONE-PIECE, SCREW-RECEIVING, EXTERNALLY-THREADED ENDOSSEOUS DENTAL IMPLANTS AND RELATED TRANSFER COMPONENTS, COMFORT CAPS AND ABUTMENTS

(76) Inventor: Gerald A. Niznick, Las Vegas, NV (US)

( * ) Notice: Subject to any disclaimer, the term of this patent is extended or adjusted under 35 U.S.C. 154(b) by 0 days.

(21) Appl. No.: 12/660,986

(22) Filed: Mar. 9, 2010

(65) Prior Publication Data

US 2010/0311013 A1 Dec. 9, 2010

(51) Int. Cl.
*A61C 8/00* (2006.01)
(52) U.S. Cl. ........................................................ 433/174
(58) Field of Classification Search .................. 433/173, 433/174
See application file for complete search history.

(56) References Cited

U.S. PATENT DOCUMENTS

| | | | |
|---|---|---|---|
| 4,960,381 A | 10/1990 | Niznick | |
| 4,998,881 A | 3/1991 | Lauks | |
| 5,246,369 A | 9/1993 | Poulmaire | |
| 5,282,746 A * | 2/1994 | Sellers et al. | 433/172 |
| 5,316,477 A * | 5/1994 | Calderon | 433/173 |
| 5,368,483 A * | 11/1994 | Sutter et al. | 433/173 |
| 5,588,838 A | 12/1996 | Hansson et al. | |
| 5,636,989 A | 6/1997 | Somborac et al. | |
| 5,702,346 A | 12/1997 | Lazzara | |
| 5,782,918 A | 7/1998 | Klardie et al. | |
| 5,816,812 A | 10/1998 | Kownacki et al. | |
| 5,829,977 A * | 11/1998 | Rogers et al. | 433/172 |
| 5,882,200 A * | 3/1999 | Sutter et al. | 433/173 |
| 5,967,783 A | 10/1999 | Ura | |
| 5,989,028 A | 11/1999 | Niznick | |
| 5,997,299 A | 12/1999 | Unger | |
| 6,039,568 A | 3/2000 | Hinds | |
| 6,247,932 B1 | 6/2001 | Sutter | |
| 6,332,777 B1 * | 12/2001 | Sutter | 433/173 |
| 6,464,500 B1 | 10/2002 | Popovic | |
| 6,508,650 B2 * | 1/2003 | Gittleman | 433/172 |
| 6,626,911 B1 | 9/2003 | Engman et al. | |
| 6,672,872 B2 | 1/2004 | Cottrell | |
| 6,824,386 B2 * | 11/2004 | Halldin et al. | 433/173 |
| 7,699,613 B2 * | 4/2010 | Niznick | 433/174 |
| 7,785,107 B2 * | 8/2010 | Niznick | 433/173 |
| 2003/0054319 A1 | 3/2003 | Gervais et al. | |
| 2003/0228556 A1 | 12/2003 | Giorno | |
| 2004/0010808 A1 | 1/2004 | deCarmo | |
| 2005/0233281 A1 | 10/2005 | Gittleman | |
| 2006/0003290 A1 | 1/2006 | Niznick | |

FOREIGN PATENT DOCUMENTS

WO   WO-02/45615 A1   6/2002

* cited by examiner

*Primary Examiner* — Ralph Lewis
(74) *Attorney, Agent, or Firm* — Patrick Bright

(57) ABSTRACT

A one-piece, screw-receiving, externally-threaded endosseous dental implant includes a body portion with external threading and, at its proximal end, an unthreaded, cylindrical portion including a retentive groove for engaging a complementary transfer component or comfort cap; a one-or two-piece screw-receiving implant abutment for attachment to a one or two-piece implant, including a retentive groove for engaging a complementary transfer component or comfort cap; and a fixture mount for insertion in a one-piece implant, that can be sectioned with the distal end used to extend the implant height.

1 Claim, 5 Drawing Sheets

ONE-PIECE, SCREW-RECEIVING, EXTERNALLY-THREADED ENDOSSEOUS DENTAL IMPLANTS AND RELATED TRANSFER COMPONENTS, COMFORT CAPS AND ABUTMENTS

This invention relates to one-piece, screw-receiving, externally-threaded endosseous dental implants. The invention also relates to snap-on plastic transfers, snap-on comfort caps and abutments for use with these implants, and with one or two-piece abutments that attach to two-piece endosseous dental implant. The two-piece abutments include a fixation screw that passes through a longitudinal passage inside the abutment. The one-piece abutments include an internal passage or chamber with an opening at the proximal end of the abutment. The passage or chamber extends distally inside the abutment and terminates inside the abutment. The passage or chamber includes, at or near the entrance to the passage or chamber, a threaded region. The passage/chamber also includes one or more multi-sided, multi-lobed or other wrench-engaging surface, e.g. for receiving an insertion tool of complementary shape and size.

These implants may also include an internal passage or chamber with an opening at the proximal end of the implant. The passage or chamber extends distally inside the body portion, and terminates inside the body portion. The passage or chamber includes, at or near the entrance to the passage or chamber, one or more multi-sided, multi-lobed or other wrench-engaging surface, e.g., for receiving an insertion tool of complementary shape and size. The passage/chamber also includes a threaded region distal to the wrench-engaging surfaces.

The externally-threaded, one-piece endosseous dental implants comprise an elongated, tapered or straight body, and, optionally, a distal self-tapping feature. The proximal end of the body of these implants may comprise an unthreaded cylindrical portion, and an outwardly extending, unthreaded region that forms a flat peripheral shoulder near the proximal end of the implant. Atop the implant is a proximally-extending, inwardly-tapering frusto-conical portion that comprises a retentive groove. This groove extends wholly or completely around the frusto-conical portion.

These implants may also include an internal passage or chamber with an opening at the proximal end of the implant. The passage or chamber extends distally inside the body portion, and terminates inside the body portion. The passage or chamber includes, at or near the entrance to the passage or chamber, one or more multi-sided, multi-lobed or other wrench-engaging surface, e.g., for receiving an insertion tool of complementary shape and size. The passage/chamber also includes a threaded region distal to the wrench-engaging surfaces.

The transfer components and comfort caps for use with these implants and abutments may include a hollow, internal, longitudinal passage. The inner surface of the passage in these caps and transfers may include a circumferential protrusion of size and shape appropriate to engage the retentive groove on the frusto-conical portion of the implants. The transfer and comfort caps may be made of a plastic material, such as nylon or ultra high molecular weight polypropylene.

The comfort cap may be cylindrical, closed at its proximal end and open to an internal passage at its distal end. The diameter of the comfort cap is preferably sufficiently large to fit over the frusto-conical portion at the proximal end of the implants or abutments, with the distal end of the cap seating on the flat peripheral shoulder near the proximal end of the implant or the abutment. When so seated, the protrusion inside the comfort cap engages the retentive groove on the frusto-conical portion of the abutment or the implant, sealing the opening to the internal passage/chamber of the implant and preventing the ingress of tissue or fluid into the internal passage/chamber. The outer surface of the cap may be smooth to avoid irritation to the tongue.

The transfer components for use with these implants and abutments, are preferably made of a plastic, such as nylon. The transfers may comprise, at their distal end, a cylindrical body portion, an internal passage of sufficient size and shape to fit over the frusto-conical portion of the implant, and a distal end surface that sits on the flat peripheral shoulder of the implant. When so seated, the circumferential or partly circumferential protrusion on the inside surface of the cap at its distal end portion engages the retentive groove on the frusto-conical portion of the implant.

The transfer components may also include, at or near their proximal end, two or more spaced-apart generally elliptical-shaped portions, and, distal to these portions, supporting flanges and cylindrical openings into the sidewall of the component. These cylindrical openings provide retention for engagement of impression material.

The one-piece abutments for use with these implants and with two-piece endosseous dental implants includes a threaded distal shank, an unthreaded middle portion proximal to the threaded shank, and a proximal end portion of size and shape complementary to the size and shape of the top portion of the implant, e.g, a female frusto-conical portion. The proximal end may be of a size and shape complementary to the size and shape of the top portions of other implants with internal wrench-engaging features such as the implants disclosed in the patents/patent applications listed below. The proximal end of these abutments may include a frusto-conical portion that is the same size and shape as the frusto-conical proximal portion of the implant, and may also include a peripheral groove on the frusto-conical portion.

The fixture mounts for use with these implants may include a distal portion that fits over, and is complementary in size and shape to the proximal end of the implant. The proximal portion of these mounts may include internal surfaces, external surfaces, or both, with one or more flat areas, or grooves for engaging installation tools. The junction of the proximal and distal portions of these mounts may be a scored, or otherwise weakened, region to permit separation of the proximal portion from the distal portion of the mounts. Upon separation, the distal portion serves to extend the height of the implant. The fixture mount may provide appropriate undercuts and flat areas in the proximal portion to allow the fixture mount to function as a transfer element.

These implants may also include one or more of the features of the endosseous dental implants, abutments and other related products, disclosed in the following U.S. Patents and Patent Applications:

U.S. patent application/Ser. No. 11/047,960, filed Feb.1, 2005 in the PTO, now U.S. Pat. No. 7,785,107, entitled "Externally-Threaded Endosseous Dental Implants With Internal Abutment-Engaging and Fixture Mount Engaging Surfaces".

U.S. patent applicaticin/Ser. No 11/047,959, filed Feb 1, 2005 in the PTO, now U.S. Pat.No. 7,677,891, entitled "Tapered Endosseous Dental Implants With External Multiple Threads".

U.S. patent application/Ser. No. 10/877,460, filed Jun. 25, 2004 in the PTO, now U.S. Pat. No. 7,108,510, entitled "Endosseous Dental Implant".

U.S. patent application/Ser. No. 10/883,275, filed Jul. 1, 2004 in the PTO, entitled "Endosseous One-Piece Screw-Type Dental Implants".

U.S.patent application/Ser. No. 101741,023, filed Dec. 19, 2003 in the PTO, now U.S. Pat. No. 7,014,464, entitled "Multi-Part Abutment and Transfer Cap for Use with An Endosseous Dental Implant with Non-Circular, Beveled Implant Abutment Interface".

U.S. patent application/Ser. No. 10/741,061, filed Dec. 19, 2003 in the PTO, now entitled "Endosseous Dental Implant", and U.S. Pat. No. 4,960,381, issued Oct. 02, 1990, entitled "Screw-Type Dental Implant Anchor."

BRIEF DESCRIPTION OF THE DRAWINGS

The invention can better be understood by reference to the drawings in which.

DETAILED DESCRIPTION OF THE DRAWINGS

Figures 1, 2, 3:
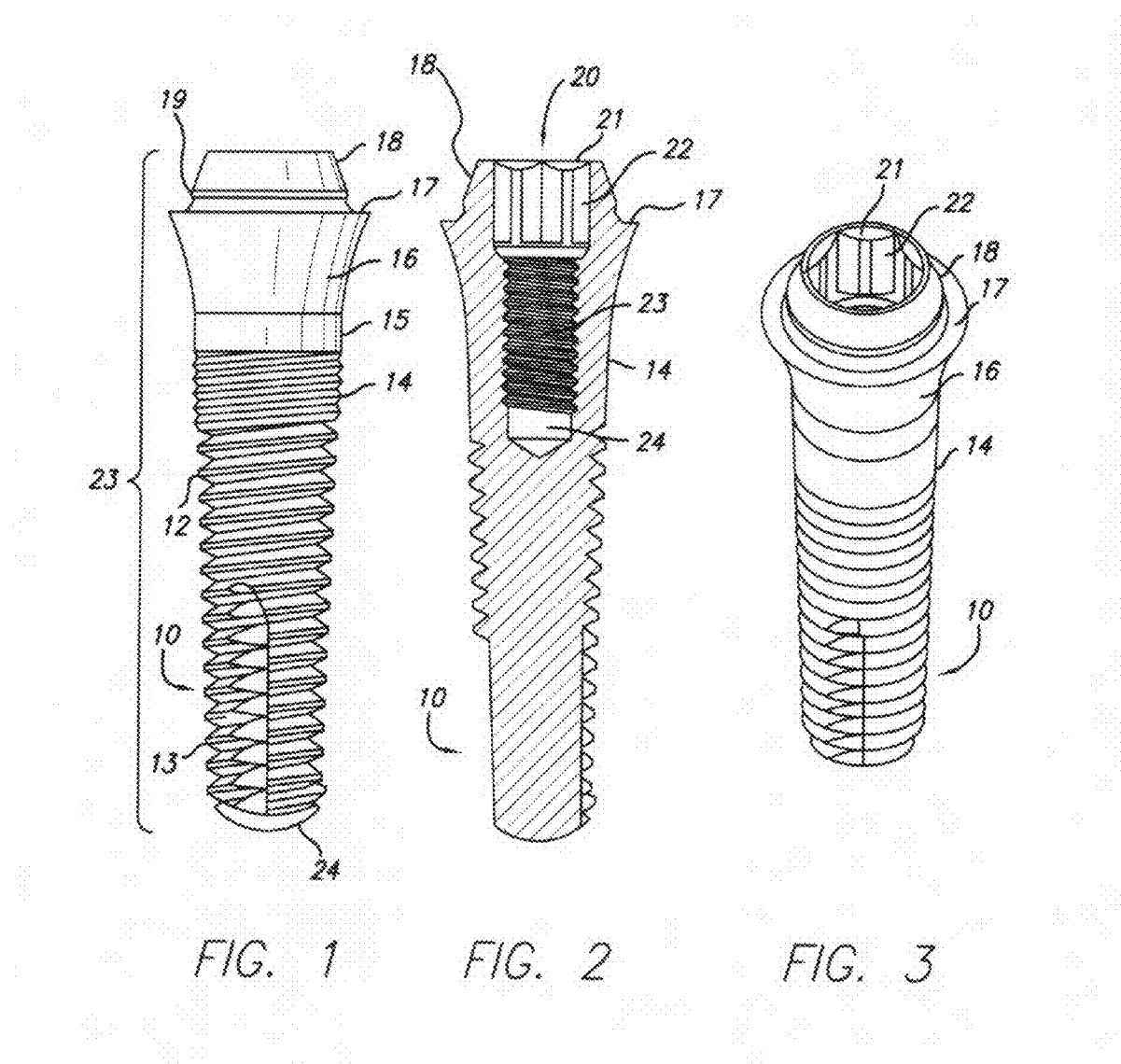
FIG. 1 shows a side elevation view of an embodiment of a one-piece, Screw-receiving, externally-threaded endosseous dental implant.
FIG. 2 shows a side elevation view, in vertical cross section, of the dental implant of FIG. 1.
FIG. 3 shows a perspective view of the dental implant of FIG. 1.

FIGS. 1,2 and 3 show an embodiment of a one-piece, screw-receiving, externally-threaded endosseous dental implant 10. Implant 10 includes body 23 that comproses a rounded, distal end 24, external thread portions 12 and 14 of different, multiple leads and a self-tapping cutting portion 13. Proximal to threaded region 14 is cylindrical unthreaded portion 15. Proximal to portion 15 is outwardly flaring, unthreaded portion 16, including, at it proximal end, circumferentially-extending flat shoulder 17. Atop shoulder 17 is inwardly tapering frusto-conical portion 18 that includes circumferential groove 19.

Frusto-conical portion 18 includes opening 20 into an internal passage inside the body of implant 10. The passage includes, at the opening to the passage, lead in bevel/chamfer 21, and below bevel/chamfer 21, multi-sided, wrench engaging surfaces 22. Distal to multi-sided, wrench-engaging surfaces 22 is internally-threaded region 23, which is shown with a smaller diameter than wrench engaging surface 22, but may be made with a diameter that is the same as the wrench-engaging surfaces. The internal passage terminates inside the body portion at unthreaded region 24.

Figures 11, 12, 13:
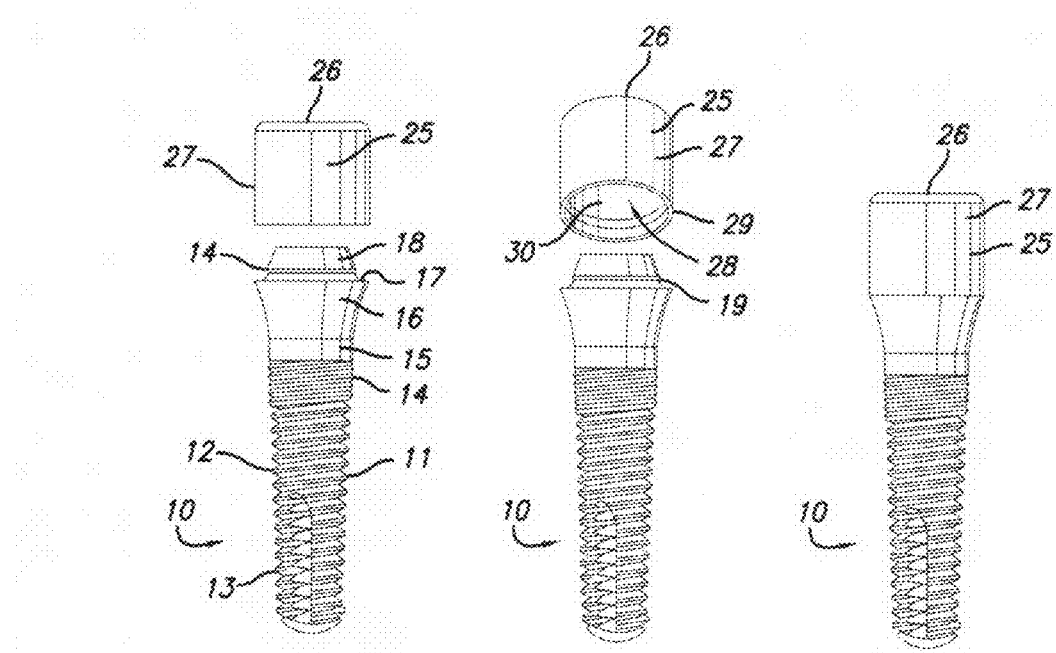
FIG. 11 shows a side elevation view of the dental implant of FIGS. 1-10, with a comfort cap positioned above the implant.
FIG. 12 shows a side elevation view of the dental implant and comfort cap of FIG. 11, with the transfer component shown in partial perspective view.
FIG. 13 shows a side elevation view of the dental implant of FIGS. 11 and 12, with the comfort cap in place atop the implant.

FIGS. 11, 12 and 13 show dental implant 10 from FIGS. 1,2 and 3, with comfort cap 25 positioned above implant 10. Cap 25 has a closed flat surface at its proximal end 26, a cylindrical sidewall 27, and an internal passage 28. The distal surface of cap 25 is a flat, circumferentially-extending surface 29 that seats, on and seals with flat shoulder 17 atop implant 10. Inside cap 25 is circumferentially-extending protrusion 30 that snaps into and engages groove 19 atop implant 10 when comfort cap 25 is in place atop implant 10 as shown in FIG. 13.

Figures 14, 15, 16:
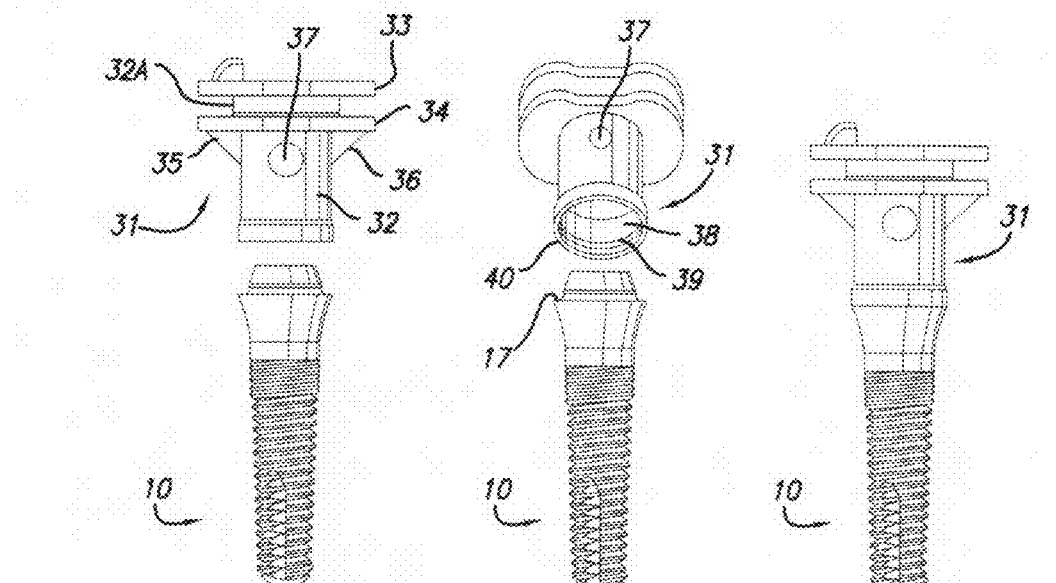
FIG. 14 shows a side elevation view of the dental implant of FIGS. 1-13, with the comfort cap positioned above the implant.
FIG. 15 shows the dental implant and transfer component of FIG. 14, with the comfort cap shown in partial perspective view.
FIG. 16 shows the dental implant and transfer component of FIGS. 14 and 15, with the comfort cap in place atop of the implant.

FIGS. 14, 15 and 16 show implant 10 and fixture mount 31 positioned above implant 10. Fixture mount 31 includes cylindrical body 32, flanges 33 and 34, integrally formed with fixture mount 31 and spaced apart by body portion 32A. Flange 34 includes supporting triangular-shaped struts 35 and 36. Sidewall 32 of component 31 also includes one r more round opening 37.

FIG. 15 shows internal passage 38 within fixture mount 31, with circumferential protrusion 39 on the inner surface of passage 38 near the opening to passage 38. Distal end 40 of fixture mount 31 is a flat, circumferentially-extending surface that is complementary in size and shape to shoulder 17 on implant 10. FIG. 16 shows fixture mount 31 in place atop implant 10, with flat surface 40 at the distal end of fixture mount 31 seated on shoulder 17 of implant 10.

Figure 4:
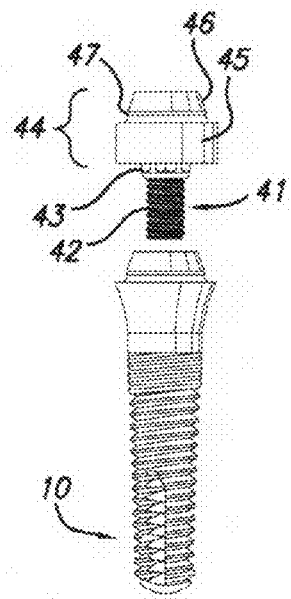
FIG. 4 shows a side elevation of view of the dental implant of FIGS. 1-3, with an abutment for use with this implant that duplicates the proximal end of the distal implant.
Figure 5:
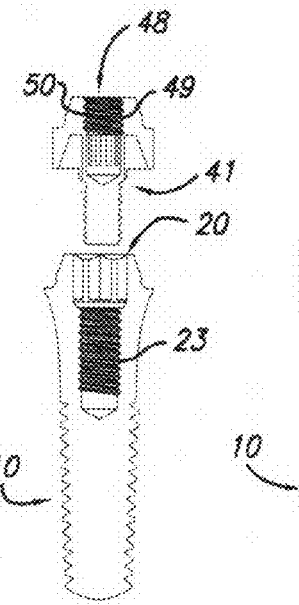
FIG. 5 shows a side elevation view of the dental implant and abutment of FIG. 4 in vertical cross section.
Figure 6:
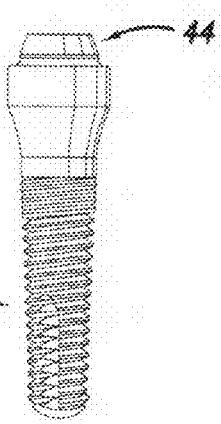
FIG. 6 shows a side elevation view of the dental implant and abutment of FIG. 4 with the abutment in place atop the implant.

FIGS. 4, 5 and 6 show dental implant 10, with abutment 41. Abutment 41 includes distal threaded shank 42, and, proximal to shank 42, unthreaded cylindrical region 43. Proximal to shank portion 43 is top portion 44 that includes an unthreaded cylindrical portion 45, and proximally-extending, inwardly-tapering, frusto-conical portion 46, with circumferential groove 47. Proximal portion 44 includes internal passage 48, which comprises internal threads 49 and internal wrench-engaging surfaces 50, distal to threads 49. Abutment 41 can be screwed into the internal passage 20 inside implant 10 with the threads of shank 42 engaging the internal threads 23 of implant 10, resulting in attachment of abutment 41 to implant 10, as shown in FIG. 6.

Figures 7, 8, 9, 10:
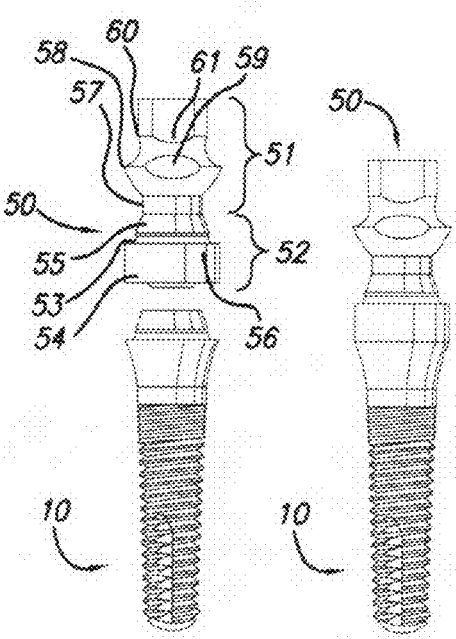
FIG. 7 shows a side elevation view of the dental implant of FIGS. 1-6, with a fixture mount positioned above the implant.
FIG. 8 shows the dental implant and transfer element of FIG. 7, with the fixture mount in place atop the implant.
FIG. 9 shows the dental implant and fixture mount component of FIG. 8 with a portion of the transfer component separated from and removed from the implant/fixture mount combination.
FIG. 10 shows a side elevation view of the dental implant of FIGS. 7 and 8, with the fixture mount shown if FIGS. 7 and 8, in vertical cross section.

FIGS. 7, 8, 9 and 10 shows dental implant 10 with fixture mount 50. Fixture mount 50 includes two separable portions 51 and 52 joined by weakened score line 53. As FIG. 9 shows, portions 51 and 52 can be separated from one another along score line 53. Portion 52 includes cylindrical sidewall portion 54 and, proximal thereto, proximal-extending, inwardly-tapering portion 55, including circumferentially-extending groove 56.

Portion 51 of fixture mount 50 includes distal, cylindrical portion 57, outwardly tapering portion 58, grooved region 60, and wrench-engaging surfaces 61 at the proximal end of portion 51. Internal to fixture mount 50 is internal passage 62, including wrench-engaging surfaces 63, at the proximal end of passage 62. The distal end of fixture mount 50 includes circumferential, frusto-conical portion 52 comprising groove 66 of size and shape complementary to the frusto-conical portion atop implant 10. With fixture mount 50 atop implant 10, the distal end of fixture mount 50, including circumferential cavity 65, seats on the proximal end of implant 10, with flat surface 64 on shoulder 17 of implant 10.

Figure 17:
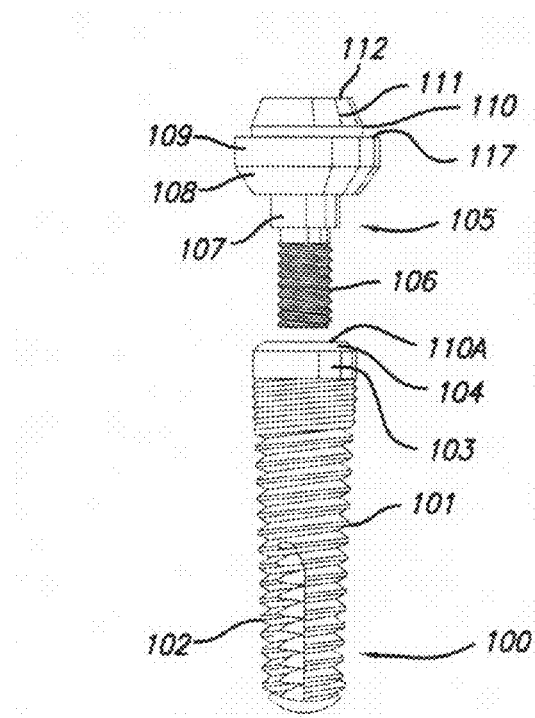
FIG. 17 shows a side elevation view of a two-piece endosseous dental implant with an abutment for use with this implant that includes, at its proximal end, a frusto-conical protion with a wholly or partly circumferential groove suitable for engaging a snap-on transfer component or a snap-on comfort cap.
Figure 18:
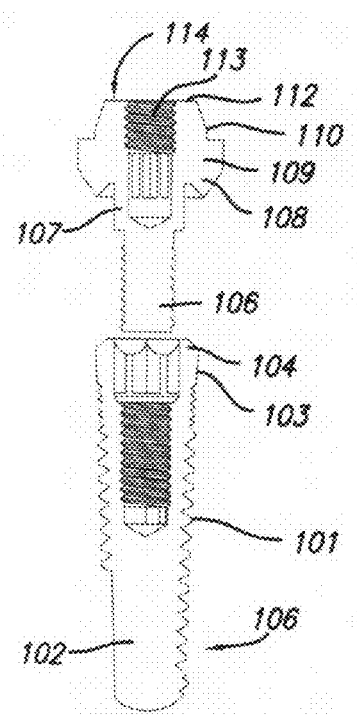
FIG. 18 shows the implant and abutment of FIG. 17, with the abutment shown in vertical cross section to expose internal threads and internal wrench-engaging surfaces in a passage inside the abutment.

FIGS. 17 and 18 show, in side elevation views, endosseous dental implant 100, having a tapered externally-threaded body 101 with a self-tapping feature 102 at the distal end of body 101. Body 101 includes a proximal, cylindrical, unthreaded portion 103 and a proximal, unthreaded, upwardly projecting, inwardly-tapering portion 104. Proximal surface 116 of implant 100 includes an opening into an internally-threaded passage. Positioned above implant 100 is abutment 105, which includes threaded distal shank 106 and unthreaded distal shank portion 107 atop shank 106. The proximal end of abutment 105 includes downwardly-extending, inwardly-tapering surface 108 distal to cylindrical, unthreaded portion 109, and circumferential shoulder 117. Frusto-conical portion 111 includes flat upper surface 112, and wholly or partly circumferential groove 110.

FIG. 18 shows, in vertical cross-section, the internal structure of abutment 105, including an internal passage with an opening at proximal surface 112. Passage 114 inside abutment 105 includes a proximal threaded region 113 and unthreaded, wrench-engaging surfaces 115 distal to threads 113.

Figure 19:
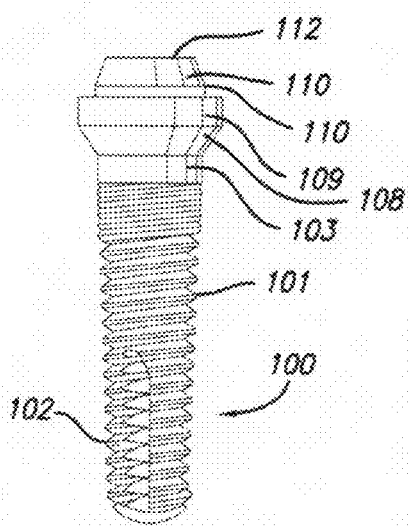
FIG. 19 shows a side elevation view of the endosseous dental implant and abutment of FIGS. 17 and 18, with the abutment in place atop the implant.
Figure 20:
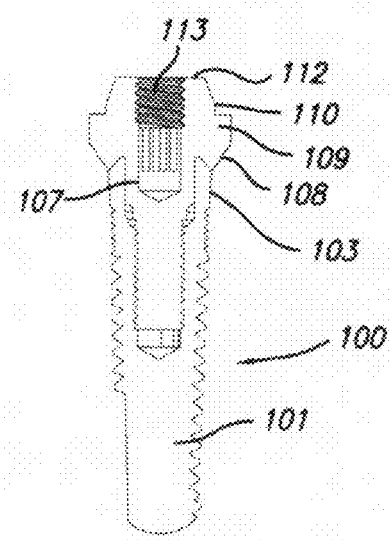
FIG. 20 shows the implant and abutment of FIG. 19 in side elevation cross-section.

FIG. 19 shows implant 100 abutment 105 screwed into place inside abutment 100. FIG. 20 shows implant 100 with abutment 105 screwed into place inside 100, as in FIG. 19, but with abutment 105 shown in side elevation cross-section.

Figures 21, 22:
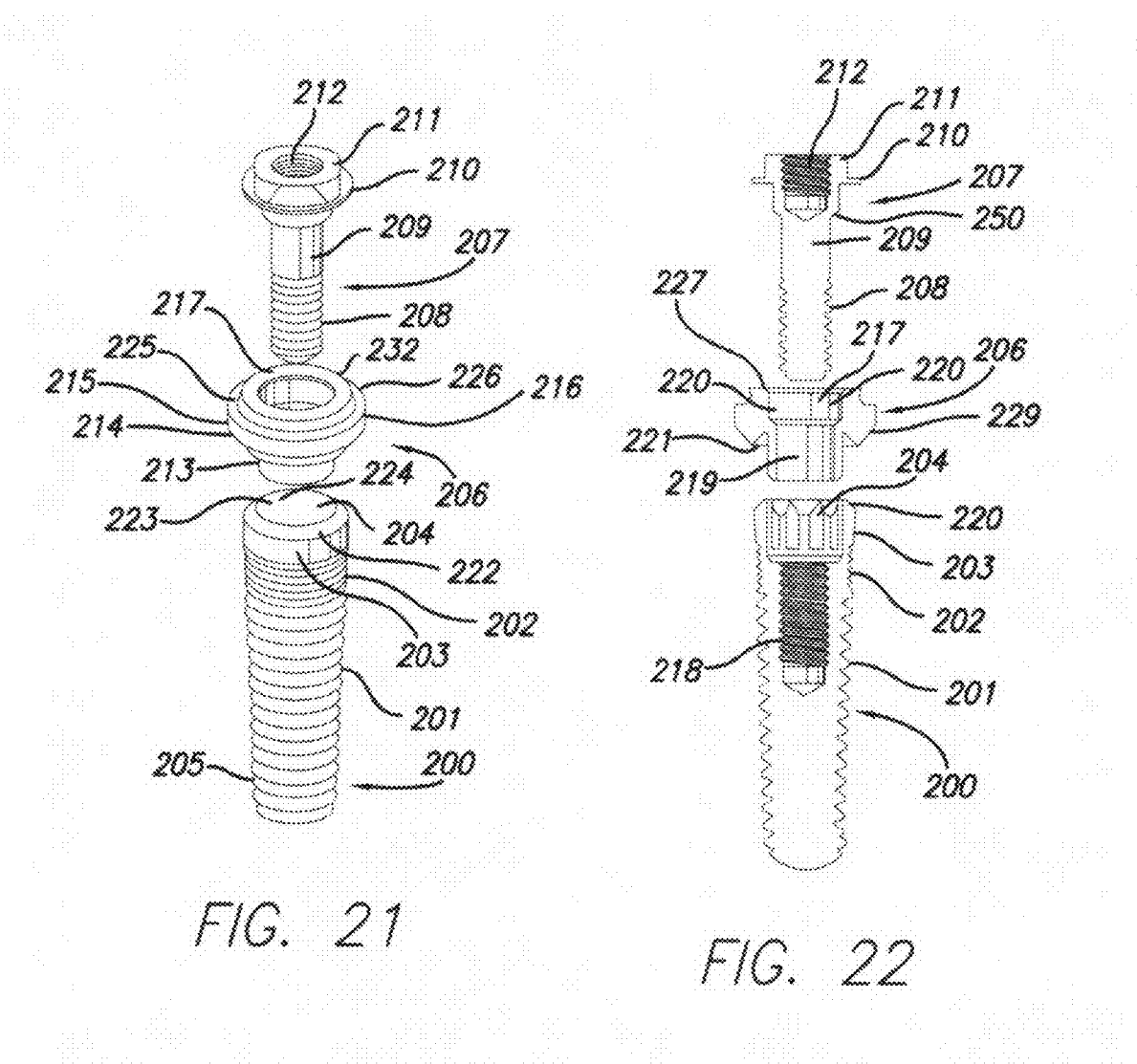
FIG. 21 show a perspective view of an endosseous dental implant and of a two-piece abutment adapted to receive a snap-on transfer component or a snap-on comfort cap.
FIG. 22 shows a side elevation view, in vertical cross-section, of the Implant/two-piece abutment assembly show in FIG. 21.

FIGS. 21 and 22 show endosseous dental implant 200 and two-piece abutment 206/207 for use with implant 200. Implant 200 includes, on its external surface, self-tapping, cutter region 205, first threaded region 201 and second threaded region 202. Proximal to the threaded regions 201 and 202 is unthreaded, cylindrical body portion 203 that includes flat, tapered surface 222 surrounding the opening to internal passage 223. Inside, at the threshold of internal passage 223 are multi-sided, wrench-engaging surfaces 204, which include lead-in chamfer 224.

See FIG. 22, showing that internal passage 223, which terminates inside implant 200, includes internally-threaded region 218.

First abutment part 206 includes, at its distal end, a multi-sided male projection 214 that is complementary in size and shape to internal wrench-engaging surfaces 204 of implant 200. Projection 214 is adapted to seat, anti-rotationally, in multi-sided wrench engaging surfaces 204. Proximal to distal portion 214 are cylindrical, unthreaded body portion 215, flat proximal shoulder 225, frusto-conical portion 226, including circumferential groove 216, and flat proximal end surface 227. End surface 227 surrounds an opening to internal, longitudinal passage 217 inside first abutment part 206.

As FIG. 22 shows, internal passage 217 includes a first cylindrical, unthreaded region of a larger diameter 228, internal flange/shelf 229, and a second cylindrical, unthreaded portion 219, smaller in diameter than region 228.

Second abutment part 207 includes distally-threaded shank 209 with threads in region 208. Atop second abutment part 207 are shoulder 210 and hexagonal portion 211. Opening 212 includes internal threads for receiving an insertion tool to screw second abutment part 207 into the internal passage 223 of implant 200.

The two-part abutment 206/207 is affixed to implant 200 by placing distal portion 214 of first abutment part 206 into the internal wrench-engaging surfaces 204 of implant 200. Fixation screw 207 is then inserted through the longitudinal passage in first abutment part 206, and threaded shank portion 208 is screwed into internal threads 218 of implant 200. Flange 210 of second abutment part 207 then egages the upper surface 227 of first abutment part 206, and external shoulder 250 on second part 206 engages internal shoulder 220 inside implant 200, holding second abutment part 206 in place atop implant 200.

The circumferential groove 216 on first abutment part 206 is adapted to receive and engage a snap-on comfort cap or a snap-on transfer component such as those shown in FIGS. 7-16, after insertion of the implant in a patient's jawbone, during the healing period, or for use in forming a suitable prostheses for attachment to implant 200.

The invention claimed is:

1. A one-piece, screw-receiving abutment for use with an endosseous dental implant, comprising, at its proximal end, an unthreaded cylindrical portion, and proximal to said unthreaded cylindrical portion, a frusto-conical portion with an unthreaded external surface and a retentive, circumferential groove for engaging a transfer component or a comfort cap, and a distal, partly-threaded shank of a size and shape appropriate to engage internal threads of an implant, said shank extending distally from beneath said unthreaded cylindrical portion, and said abutment including an internal passage extending distally into an opening at the proximal end of said implant, said internal passage including multi-sided, wrench-engaging surfaces and a threaded region.

* * * * *